United States Patent
Yang

(10) Patent No.: US 10,545,038 B2
(45) Date of Patent: Jan. 28, 2020

(54) ELECTRONIC DEVICES WITH ENVIRONMENTAL SENSORS

(71) Applicant: Apple Inc., Cupertino, CA (US)

(72) Inventor: Henry H. Yang, Los Gatos, CA (US)

(73) Assignee: Apple Inc., Cupertino, CA (US)

( * ) Notice: Subject to any disclaimer, the term of this patent is extended or adjusted under 35 U.S.C. 154(b) by 0 days.

(21) Appl. No.: 16/261,316

(22) Filed: Jan. 29, 2019

(65) Prior Publication Data

US 2019/0154471 A1     May 23, 2019

Related U.S. Application Data

(63) Continuation of application No. 15/722,981, filed on Oct. 2, 2017, now Pat. No. 10,209,106, which is a
(Continued)

(51) Int. Cl.
*G01D 11/30* (2006.01)
*G01D 11/24* (2006.01)
(Continued)

(52) U.S. Cl.
CPC .......... *G01D 11/245* (2013.01); *G01D 11/30* (2013.01); *G01N 33/0004* (2013.01); *H04R 1/021* (2013.01); *H04R 1/04* (2013.01); *H01L 2224/48137* (2013.01); *H01L 2224/48227* (2013.01); *H01L 2924/15192* (2013.01); *H01L 2924/16151* (2013.01); *H01L 2924/16251* (2013.01); *H04M 2250/12* (2013.01); *H04R 2499/11* (2013.01)

(58) Field of Classification Search
None
See application file for complete search history.

(56) References Cited

U.S. PATENT DOCUMENTS 6,195,572 B1     2/2001  Patterson et al.
6,868,731 B1 *   3/2005  Gatesman ............... G01L 9/125
                                                                73/714
(Continued)

FOREIGN PATENT DOCUMENTS

WO      2011087770      7/2011
WO      2011117862      9/2011

*Primary Examiner* — Jamel E Williams
(74) *Attorney, Agent, or Firm* — Treyz Law Group, P.C.; G. Victor Treyz; Joseph F. Guihan

(57) ABSTRACT

An electronic device may be provided with environmental sensors. Environmental sensors may include one or more environmental sensor components and one or more acoustic components. Acoustic components may include a speaker or a microphone. Environmental sensor components may include a temperature sensor, a pressure sensor, a humidity sensor, a gas sensor, or other sensors or combinations of sensors for sensing attributes of the environment surrounding the device. The environmental sensor may have an enclosure with an opening. The enclosure may be formed from a rigid support structure and a portion of a printed circuit. The opening may be formed in the rigid support structure or the printed circuit. The opening in the enclosure for the environmental sensor may be aligned with an opening in an outer structural member for the device. The outer structural member may be a housing structure or a cover layer for a device display.

20 Claims, 11 Drawing Sheets

Related U.S. Application Data continuation of application No. 14/687,438, filed on Apr. 15, 2015, now Pat. No. 9,804,003, which is a continuation-in-part of application No. 13/658,316, filed on Oct. 23, 2012, now Pat. No. 9,167,325.

(51) Int. Cl.
  *H04R 1/04* (2006.01)
  *G01N 33/00* (2006.01)
  *H04R 1/02* (2006.01)

(56) References Cited

U.S. PATENT DOCUMENTS

| | | | |
|---|---|---|---|
| 7,834,759 B2 | 11/2010 | Charlier et al. | |
| 7,907,931 B2 | 3/2011 | Hartigan et al. | |
| 9,167,325 B2* | 10/2015 | Yang | H04R 1/021 |
| 2006/0046787 A1* | 3/2006 | Zhu | H04B 15/02 |
| | | | 455/566 |
| 2006/0064037 A1 | 3/2006 | Shalon | |
| 2006/0185429 A1 | 8/2006 | Liu et al. | |
| 2007/0023851 A1* | 2/2007 | Hartzell | B81C 1/00246 |
| | | | 257/414 |
| 2008/0192963 A1 | 8/2008 | Sato | |
| 2008/0205668 A1* | 8/2008 | Torii | H04R 1/326 |
| | | | 381/113 |
| 2008/0279407 A1* | 11/2008 | Pahl | B81B 7/0064 |
| | | | 381/355 |
| 2008/0315333 A1* | 12/2008 | Combi | B81B 7/0061 |
| | | | 257/415 |
| 2009/0040044 A1* | 2/2009 | Chiao | A61B 5/0002 |
| | | | 340/540 |
| 2009/0127638 A1* | 5/2009 | Kilger | B81B 7/007 |
| | | | 257/415 |
| 2010/0086163 A1* | 4/2010 | Lorenz | H04R 1/2819 |
| | | | 381/353 |
| 2010/0139657 A1* | 6/2010 | Chalvignac | A61M 16/0057 |
| | | | 128/204.22 |
| 2010/0303273 A1 | 12/2010 | Sawada | |
| 2011/0062573 A1 | 3/2011 | Zhe | |
| 2011/0296900 A1* | 12/2011 | Thorson | G01N 21/1702 |
| | | | 73/24.02 |
| 2012/0040216 A1* | 2/2012 | Parakulam | G05B 19/042 |
| | | | 429/61 |
| 2012/0242592 A1 | 9/2012 | Rothkopf et al. | |
| 2012/0244848 A1 | 9/2012 | Ghaffari et al. | |
| 2013/0108082 A1* | 5/2013 | Dave | H04R 1/086 |
| | | | 381/122 |
| 2013/0294622 A1* | 11/2013 | Kasai | H04R 19/005 |
| | | | 381/162 |
| 2014/0133685 A1* | 5/2014 | Liu | H04R 7/20 |
| | | | 381/355 |
| 2015/0023523 A1* | 1/2015 | Elian | H04R 1/083 |
| | | | 381/91 |
| 2015/0204753 A1* | 7/2015 | Scheucher | G01M 3/002 |
| | | | 700/275 |
| 2016/0014488 A1* | 1/2016 | Iwaya | H04R 3/005 |
| | | | 381/91 |
| 2016/0282151 A1* | 9/2016 | Kursula | G01D 11/245 |

* cited by examiner

ELECTRONIC DEVICES WITH ENVIRONMENTAL SENSORS

This application is a continuation of patent application Ser. No. 15/722,981, filed Oct. 2, 2017, which is a continuation of application Ser. No. 14/687,438, filed Apr. 15, 2015, now U.S. Pat. No. 9,804,003, which is a continuation-in-part of patent application Ser. No. 13/658,316, filed Oct. 23, 2012, now U.S. Pat. No. 9,167,325, which are hereby incorporated by reference herein in their entireties.

BACKGROUND

This relates generally to electronic devices and, more particularly, to electronic devices with environmental sensors.

Electronic devices such as cellular telephones, portable computers, and tablet computers are sometimes provided with audio components such as microphones and speakers. Audio components are often mounted behind open ports in the device that allow sound to pass through the ports to or from the audio components.

In some situations it may be desirable to provide a device with environmental sensors such as thermometers for sensing the temperature of the environment in the vicinity of the device. Environmental sensors may require additional open ports in a device that allow interaction with the surrounding environment. However, additional open portions in a device can increase the risk of unwanted environmental materials such as moisture entering the device.

It would therefore be desirable to be able to provide improved environmental sensors for electronic devices.

SUMMARY

An electronic device may be provided with electronic components such as environmental sensors.

An environmental sensor may include multiple sensor components such as a temperature sensor, a pressure sensor, a humidity sensor, a gas sensor, a smoke detector, and a sound sensor (microphone). The sensor components may be mounted within an enclosure that at least partially surrounds the sensor components. The enclosure may have an opening that allows sound and/or other environmental materials such as air to enter the enclosure and interact with the sensor components. The enclosure may include a rigid support structure and portion of a printed circuit such as a flexible printed circuit.

The sensor components may be attached to the printed circuit. Conductive structures such as wire bonds may be used to electrically couple contact pads on the sensor components to other sensor components and/or to the printed circuit. The rigid support structure may be attached to the printed circuit and pass over the sensor components.

The opening in the enclosure for the environmental sensor may be formed in the rigid support structure or the printed circuit. The opening in the enclosure may be aligned with an opening in a housing structure for the electronic device. In this way, a device may be provided with multiple environmental sensor components and audio components while minimizing the number of open ports into the interior of the device.

If desired, an environmental sensor may include an output component such as an audio output component in the enclosure.

Further features of the invention, its nature and various advantages will be more apparent from the accompanying drawings and the following detailed description of the preferred embodiments.

DETAILED DESCRIPTION

An electronic device may be provided with electronic components such as buttons, switches, displays, speakers, microphones, and environmental sensors. Environmental sensors may be provided that include multiple sensor components and one or more audio components such as a microphone or a speaker.

The electronic device may include one or more housing structures that form a housing for the device. The housing structures may have one or more openings. The environmental sensor may have an enclosure with an opening that is aligned with an opening in the housing structures.

An electronic device may use one or more environmental sensors to gather environmental data associated with the environmental conditions surrounding the device. As an example, an electronic device may use an environmental sensor having a temperature sensor, a pressure sensor, a humidity sensor, a combined temperature and humidity sensing integrated circuit, a pressure sensor, and/or a sound sensor (i.e., a microphone) to gather environmental data such as temperature data, humidity data, pressure data and audio input data for the device.

The environmental data may be converted to user readable numbers such as a temperature, a humidity level, an air pressure value, etc. The user readable numbers may be provided to the user (e.g., using a display such as a liquid crystal display or an organic light-emitting diode display) or may be used in operating the device (e.g., control circuitry in the device may place the device in a safe mode of operation in response to a detected temperature that is outside of a predetermined safe range of operating temperatures).

Figure 1:
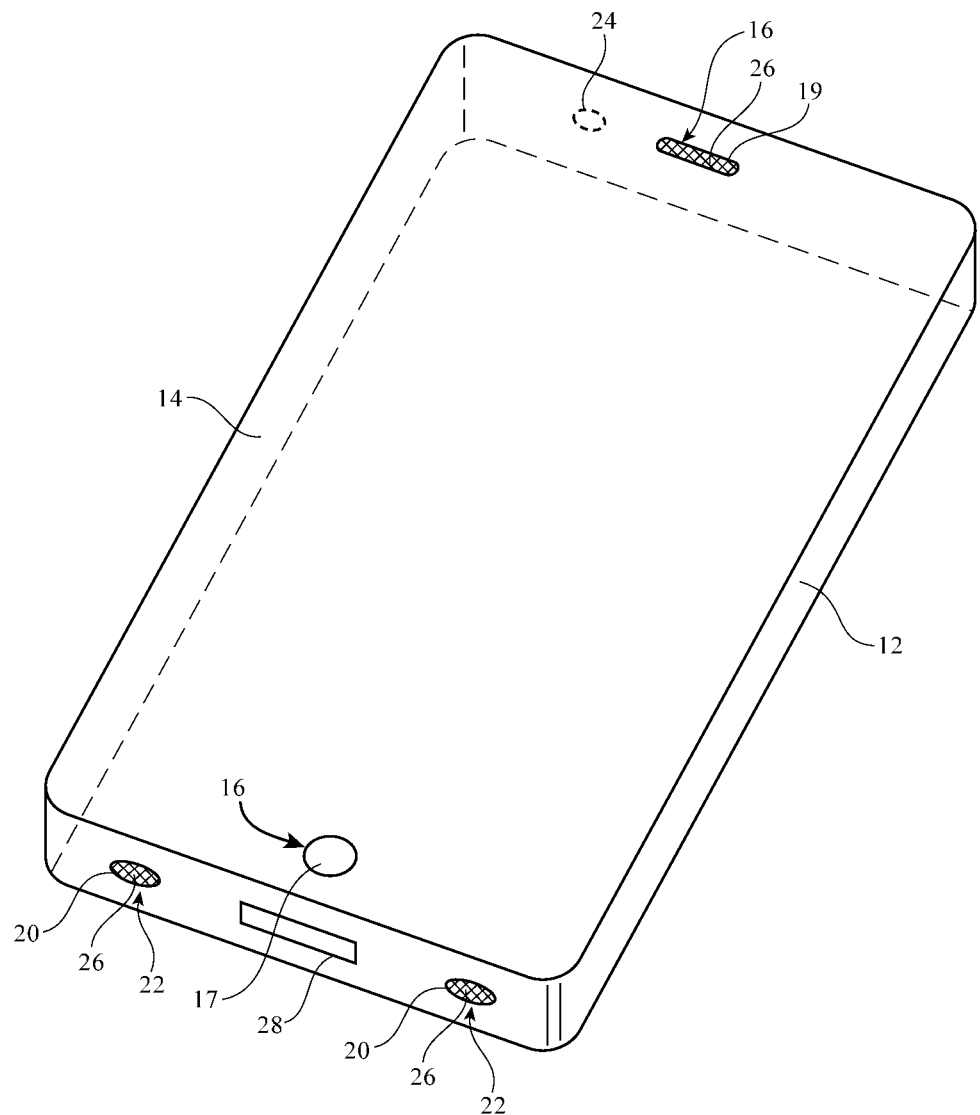
FIG. 1 is a perspective view of an illustrative electronic device with an environmental sensor in accordance with embodiments of the present invention.

An illustrative electronic device that may be provided with an environmental sensor having multiple sensor components in an enclosure is shown in FIG. 1. Electronic devices such as device 10 of FIG. 1 may be cellular telephones, media players, other handheld portable devices, somewhat smaller portable devices such as wrist-watch devices, pendant devices, or other wearable or miniature devices, gaming equipment, tablet computers, notebook computers, desktop computers, televisions, computer monitors, computers integrated into computer displays, or other electronic equipment.

As shown in the example of FIG. 1, device 10 may include a display such as display 14. Display 14 may be mounted in a housing such as housing 12. Housing 12 may have upper and lower portions joined by a hinge (e.g., in a laptop computer) or may form a structure without a hinge, as shown in FIG. 1. Housing 12, which may sometimes be referred to as an enclosure or case, may be formed of plastic, glass, ceramics, fiber composites, metal (e.g., stainless steel, aluminum, etc.), other suitable materials, or a combination of any two or more of these materials. Housing 12 may be formed using a unibody configuration in which some or all of housing 12 is machined or molded as a single structure or may be formed using multiple structures (e.g., an internal frame structure, one or more structures that form exterior housing surfaces, etc.).

Display 14 may be a touch screen display that incorporates a layer of conductive capacitive touch sensor electrodes or other touch sensor components (e.g., resistive touch sensor components, acoustic touch sensor components, force-based touch sensor components, light-based touch sensor components, etc.) or may be a display that is not touch-sensitive. Capacitive touch screen electrodes may be formed from an array of indium tin oxide pads or other transparent conductive structures.

Device 10 may have internal user interface components such as button 17 or component 19 that occupy openings such as openings 16 in an optional rigid cover layer of display 14. Component 19 may be a speaker component or may be an environmental sensor having at least one sensor component and a speaker component. Device 10 may include additional components such as components 20 that occupy openings such as openings 22 in housing 12. Components 20 may be speaker components, microphone components, environmental sensors having one or more sensor components, environmental sensors having one or more sensor components including a sound sensor component, or environmental sensors having one or more sensor components and a speaker component.

Housing 12 may be provided with additional openings such as audio port opening 24 for receiving an audio cable and connector port 28 for receiving a connector (e.g., a 30-pin connector, a universal serial bus (USB) connector, or other connector).

Openings in device 10 such as openings 22 in housing 12 and opening 16 for component 19 may be provided with a cover member such as mesh members 26 that covers the opening while allowing air and sound to flow through openings in the mesh member.

Figure 2:
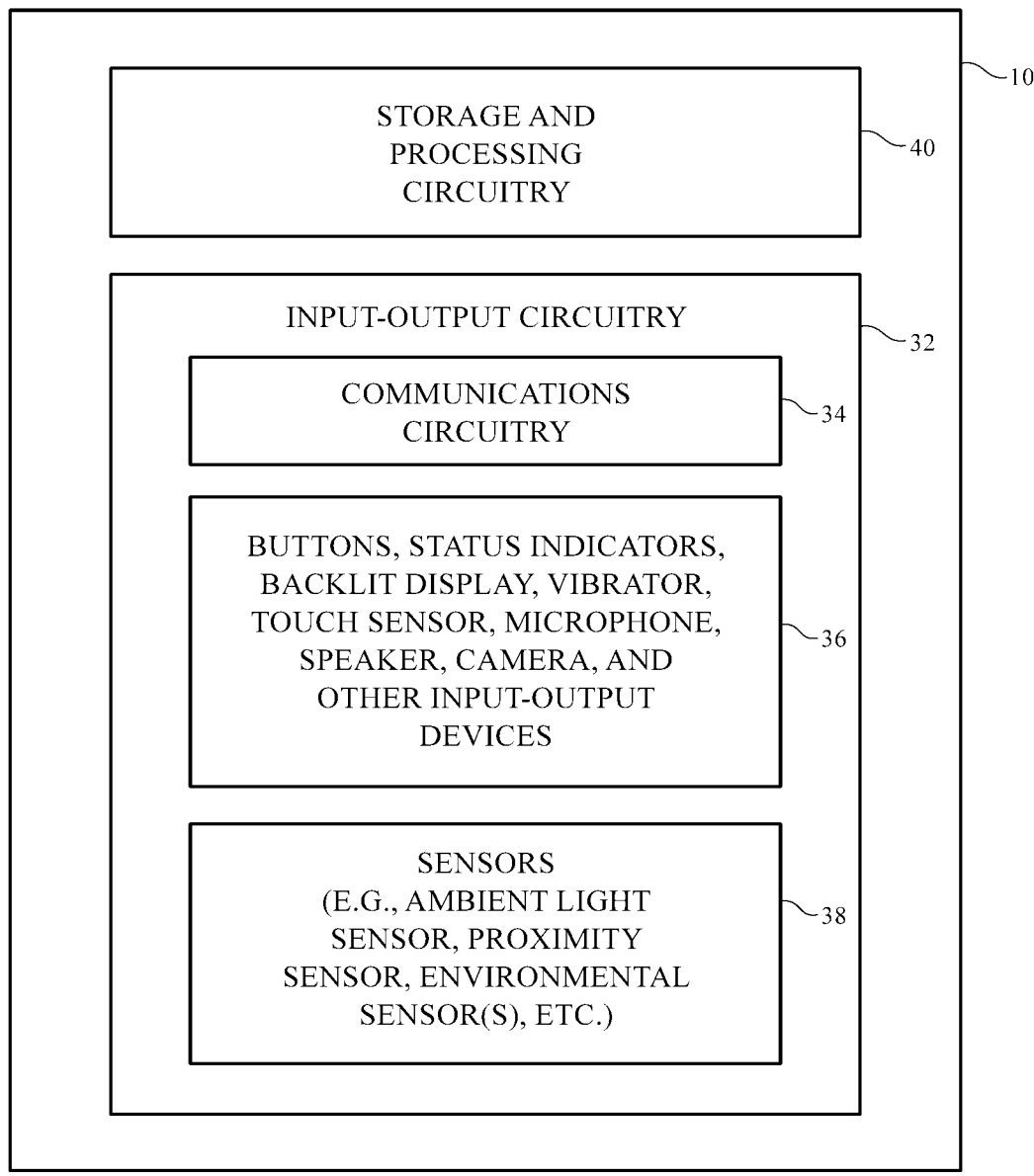
FIG. 2 is a schematic diagram of an illustrative electronic device with an environmental sensor in accordance with an embodiment of the present invention.

A schematic diagram of device 10 showing how device 10 may include environmental sensors and other components is shown in FIG. 2. As shown in FIG. 2, electronic device 10 may include control circuitry such as storage and processing circuitry 40.

Storage and processing circuitry 40 may include one or more different types of storage such as hard disk drive storage, nonvolatile memory (e.g., flash memory or other electrically-programmable-read-only memory), volatile memory (e.g., static or dynamic random-access-memory), etc. Processing circuitry in storage and processing circuitry 40 may be used in controlling the operation of device 10. The processing circuitry may be based on a processor such as a microprocessor and other suitable integrated circuits. With one suitable arrangement, storage and processing circuitry 40 may be used to run software on device 10, such as internet browsing applications, email applications, media playback applications, operating system functions, software for capturing and processing images, software implementing functions associated with gathering and processing sensor data such as temperature data, software that makes adjustments to display brightness and touch sensor functionality, etc.

Input-output circuitry 32 may be used to allow data to be supplied to device 10 and to allow data to be provided from device 10 to external devices.

Input-output circuitry 32 may include wired and wireless communications circuitry 34. Communications circuitry 34 may include radio-frequency (RF) transceiver circuitry formed from one or more integrated circuits, power amplifier circuitry, low-noise input amplifiers, passive RF components, one or more antennas, and other circuitry for handling RF wireless signals. Wireless signals can also be sent using light (e.g., using infrared communications).

Input-output circuitry 32 may include input-output devices 36 such as button 17 of FIG. 1, joysticks, click wheels, scrolling wheels, a touch screen such as display 14 of FIG. 1, other touch sensors such as track pads or touchsensor-based buttons, vibrators, audio components such as microphones and speakers, image capture devices such as a camera module having an image sensor and a corresponding lens system, keyboards, status-indicator lights, tone generators, key pads, and other equipment for gathering input from a user or other external source and/or generating output for a user.

Sensor circuitry such as sensors 38 of FIG. 2 may include ambient light sensors, proximity sensors, an accelerometer, a gyroscope, environmental sensors such as sensor packages having multiple sensor components such as a pressure sensor, a temperature sensor, a humidity sensor, a gas sensor, a smoke sensor, and a microphone, and other circuitry for making measurements of the environment surrounding device 10.

In some configurations, some of input-output components 36 and some of sensors 38 may be mounted in a common sensor package having an enclosure with an opening.

Figure 3:
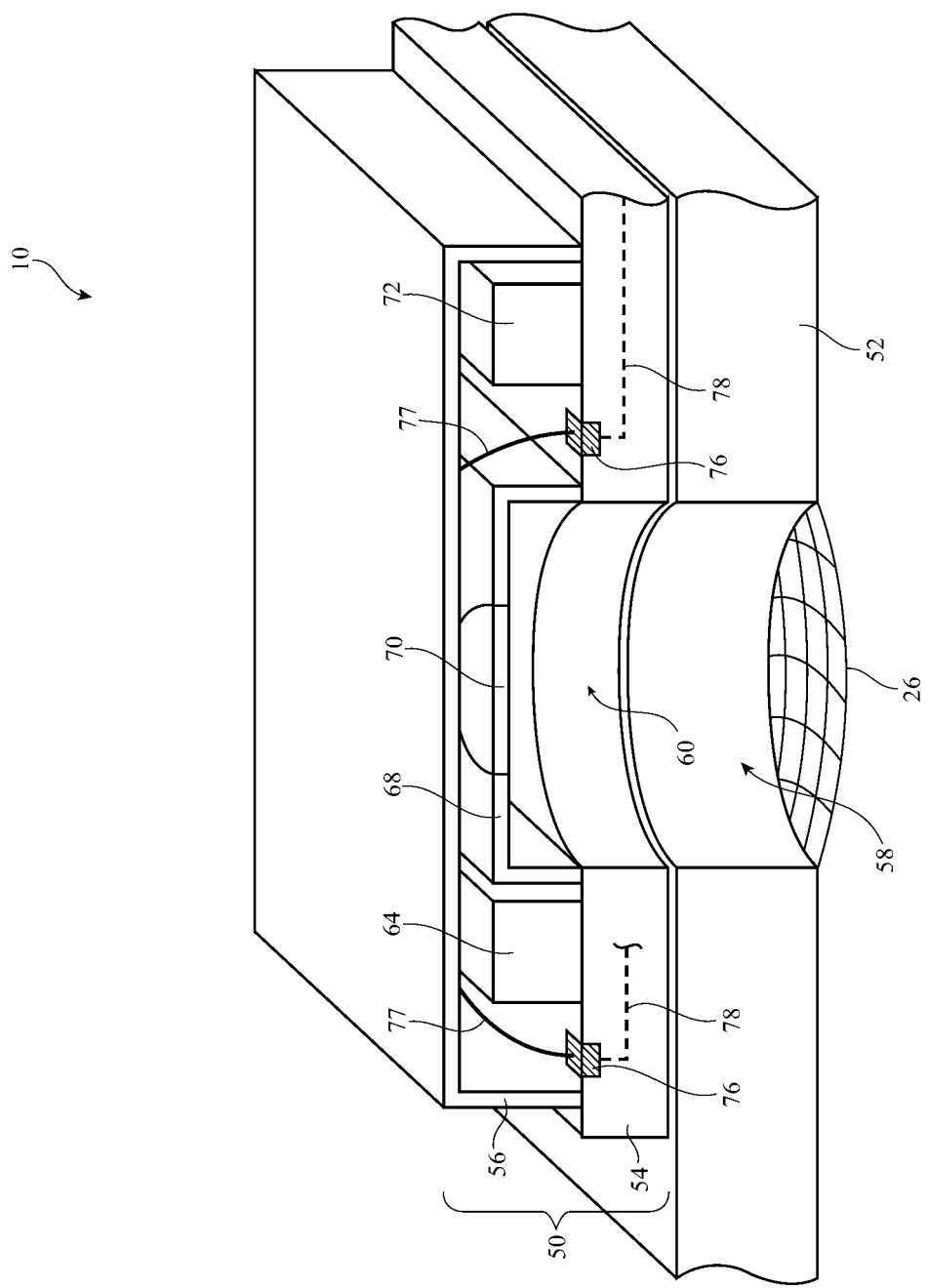
FIG. 3 is a cross-sectional perspective view of a portion of an illustrative electronic device in the vicinity of an environmental sensor having an opening in a printed circuit portion of the sensor that is aligned with an opening in an outer structural member for the device in accordance with an embodiment of the present invention.

FIG. 3 is a perspective view of a portion of device 10 in the vicinity of an environmental sensor package that is aligned with an opening in an outer device structure. As shown in FIG. 3, an environmental sensor package such as environmental sensor 50 may include sensor components such as components 64, 68, and 72 mounted to a printed circuit such as printed circuit 54. Sensor 50 may, as examples, be one of components 19 or 20 of FIG. 1. Sensor components 64, 68, and 72 may be covered by a cowling structure such as rigid support structure 56 so that components 64, 68, and 72 are formed in an enclosure formed by rigid support structure 56 and a portion of printed circuit 54.

Rigid support structure 56 may be formed from metal, plastic, ceramic, or other materials or combinations of materials. Printed circuit 54 may be formed from a rigid printed circuit board (e.g., one or more layers of fiberglass-filled epoxy with interposed conductive layers), a flexible printed circuit (e.g., one or more flexible sheets of polyimide or other flexible polymer layers having conductive traces), or a combination of rigid and flexible printed circuit layers.

Rigid support structure 56 may be attached to printed circuit 54 using adhesive (e.g., pressure sensitive adhesive, curable liquid adhesive, or other adhesive) or using mechanical attachment members such as screws, clips or clamps (as examples).

Sensor components such as components 64, 68 and 72 may be attached to printed circuit 54. Sensor components 64, 68, and 72 may be attached to printed circuit 54 using adhesive, using mechanical attachment members, or using conductive adhesive such as solder, anisotropic conductive adhesive or other adhesive materials that conductively couple components such as sensor components 64, 68, and 72 to printed circuit 54.

In configurations in which conductive adhesive attaches a component to printed circuit 54, that conductive adhesive may be used to transfer control signals to and from conductive signal lines 78 (conductive traces) in printed circuit 54 to that component. However, this is merely illustrative. If desired, printed circuit 54 may be provided with conductive contacts 76 (e.g., copper bond pads) that are formed separately from components 64, 68, and 72.

Components such as components 64, 68, and 72 may be attached to one or more other components 64, 68, or 72 or to conductive contacts 76 using, for example, wire bonds such as wire bonds 77. Wire bonds 77 may be bonded on a first end to a contact 76 and on an opposing second end to a conductive contact (not shown) on one of components 64, 68, and 72. If desired, additional wire bonds (not shown) may be used to couple a component such as one of components 64, 68 or 72 to another one of components 64, 68, and 72.

Components 64 and 72 may be environmental sensor components such as temperature sensors (i.e., thermometers), pressure sensors, humidity sensors, combination temperature and humidity sensors, or other environmental sensor components (e.g., gas sensors, smoke detectors, etc.). In one suitable example, component 64 is an integrated circuit having temperature and humidity sensing capabilities and component 72 is a pressure sensor for sensing the pressure of the air within the enclosure formed by printed circuit 54 and rigid support structure 56.

Component 68 may be an audio component (sometimes referred to as an acoustic component) such as a microphone (sometimes referred to as a sound sensor) or a speaker. Printed circuit 54 may be provided with an opening such as opening 60. Opening 60 in printed circuit 54 may be aligned with an opening such as opening 58 in an outer structural member for device 10 such as structural member 52. Structural member 52 may be a portion of housing 12 or a portion of an outer cover layer for display 14 of device 10 (see, e.g., FIG. 1). Opening 58 may, as examples, be one of openings 16 or 20 of FIG. 1. Printed circuit 54 may be attached to structural member 52 using adhesive or mechanical attachment members such as screws, clips, clamps, or other attachment members (as examples).

Opening 58 and opening 60 may allow air to flow from outside device 10 (e.g., outside of structural member 52) through openings 58 and 60 and into the enclosure for sensor 50. In this way, sensor components 64, 68, and 72 may be exposed to the environment surrounding device 10 and may therefore be used to gather temperature data, humidity data, pressure data, sound data, user input data, or other data from the surrounding environment and/or to transmit sound from sensor 50 to the surrounding environment.

As shown in FIG. 3, audio component 68 may be mounted over opening 60 in printed circuit 54. Audio component 68 may include a membrane such as permeable membrane 70. Permeable membrane 70 may move in response to electrical signals provided to component 72 from printed circuit 54 to generate sound that is transmitted out of device 10 through openings 58 and 60 or membrane 70 may move in response to sound that enters device 10 through openings 58 and 60 and component 72 may generate electrical signals in response to that movement. Permeable membrane 70 may allow air to flow through membrane 70 into other portions of the enclosure for sensor 50, thereby allowing air from the external environment of device 10 to reach additional sensor components such as sensor components 64 and 72.

Opening 58 in structural member 52 may be covered by a mesh cover such as mesh member 26. Mesh member 26 may be formed from wires that are spaced apart so that air and sound can be passed through mesh member 26 while larger objects such as dust particles are prevented from entering device 10 through opening 58.

The arrangement of FIG. 3 in which printed circuit 54 is provided with an opening that allows air to enter the enclosure for sensor 50 is merely illustrative. If desired, rigid support structure 56 may be provided with an opening that allows air to enter the enclosure for sensor 50, as shown in FIG. 4.

Figure 4:
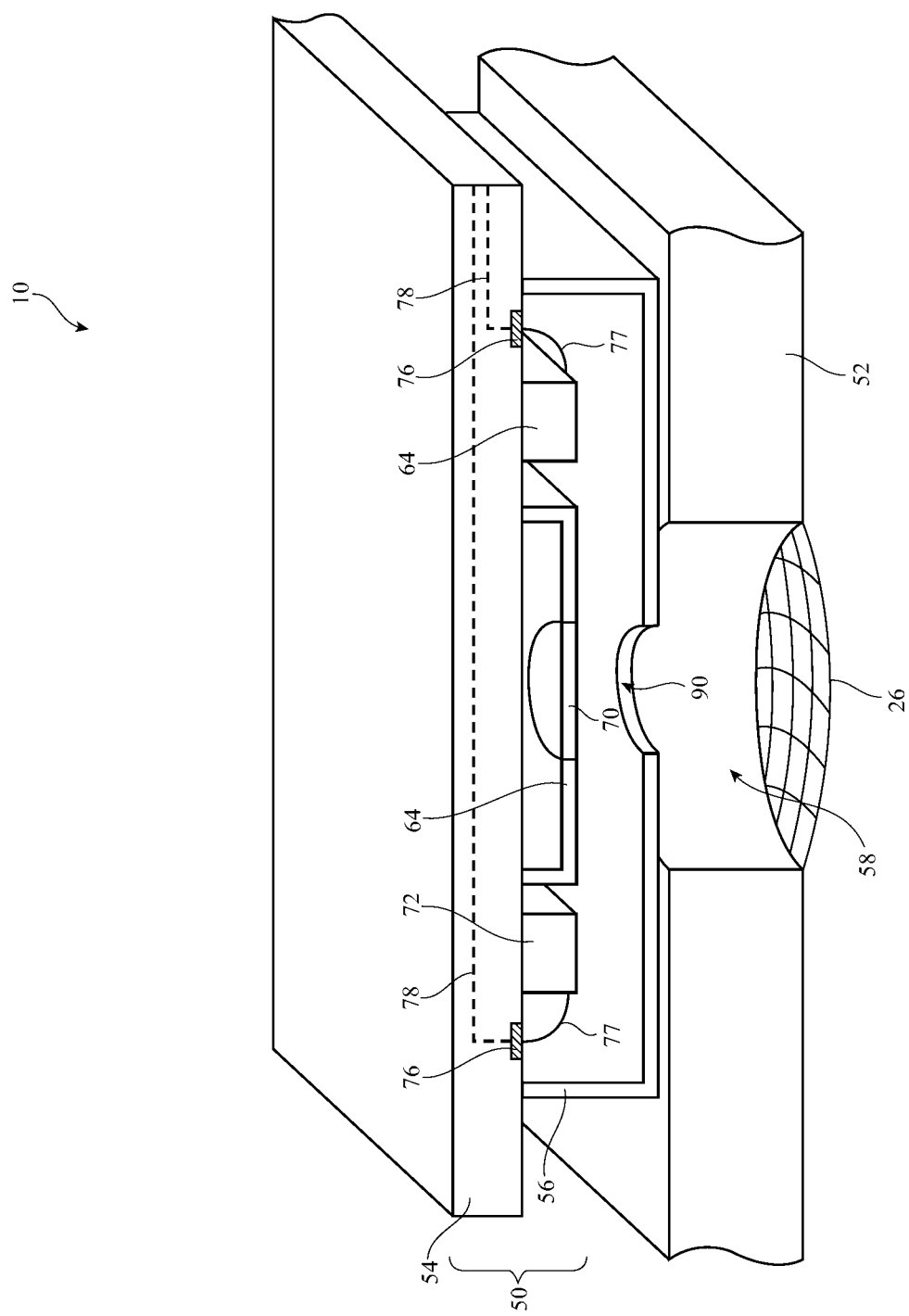
FIG. 4 is a cross-sectional perspective view of a portion of an illustrative electronic device in the vicinity of an environmental sensor having an opening in a rigid support structure of the sensor that is aligned with an opening in an outer structural member for the device in accordance with an embodiment of the present invention.

In the example of FIG. 4, rigid support structure 56 is attached to structural member 52 (e.g., a portion of housing 12 or a display cover layer for display 14). Rigid support structure 56 may be attached to structural member 52 using adhesive (e.g., pressure sensitive adhesive, curable liquid adhesive, or other adhesive) or using mechanical attachment members such as screws, clips or clamps (as examples).

Rigid support structure 56 may be provided with a hole such as opening 90. Opening 90 may be aligned with opening 58 in structural member 52 so that air may flow into the enclosure for sensor 50 (e.g., into the space between printed circuit 54 and rigid support structure 56). Permeable membrane 70 of acoustic component 68 may be aligned with opening 90 and opening 58 so that sounds generated using membrane 70 may pass through opening 90 and opening 58 or sounds generated outside of device 10 such as a user's voice may pass through opening 90 and opening 58 to move membrane 70.

Figure 5:
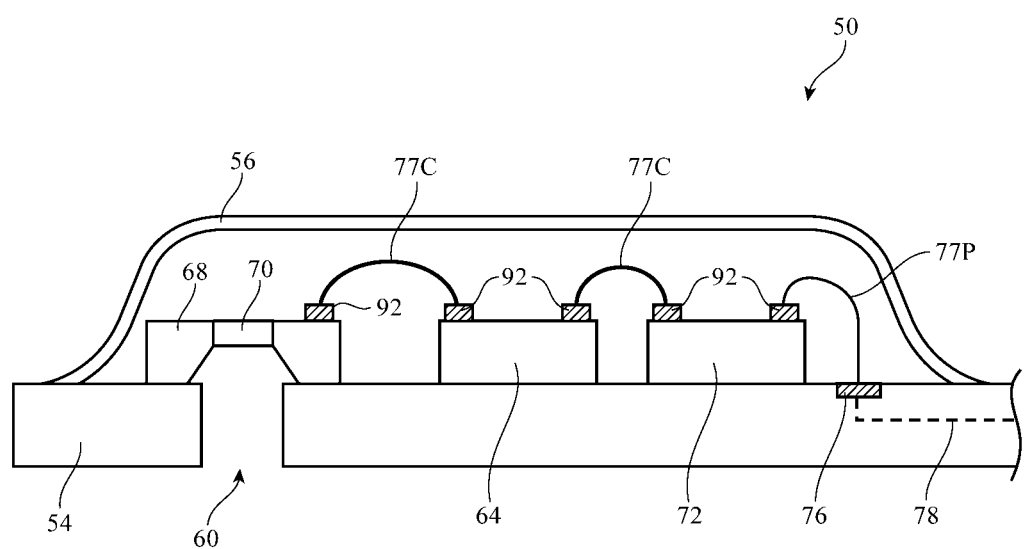
FIG. 5 is a cross-sectional side view of an illustrative environmental sensor having an opening in a printed circuit portion of the sensor showing how sensor components may be wire bonded to other sensor components in accordance with an embodiment of the present invention.

FIG. 5 is a cross-sectional side view of environmental sensor 50 in a configuration in which sensor components such as components 64, 68, and 72 are mounted to a printed circuit having an opening 60, showing how the sensor components may be coupled to each other and to the printed circuit using wire bonds 77. As shown in FIG. 5, sensor components 64, 68, and 72 may have one or more conductive contacts 92 (e.g., copper bond pads) formed on a surface of the component.

One of wire bonds 77 may be bonded to each contact 92. Sensor 50 may include wire bonds 77C that electrically couple a first sensor component to a second sensor component and wire bonds 77P that electrically couple a sensor component to one of contacts 76 on printed circuit 54. In the example of FIG. 5, a wire bond 77C is coupled between contacts 92 on acoustic component 68 and sensor component 64 (e.g., a temperature sensor, a humidity sensor, or a temperature and humidity sensing integrated circuit) and an additional wire bond 77C is coupled between contacts 92 on sensor component 64 and sensor component 72 (e.g., a pressure sensor). In this way, multiple sensor components may be electrically coupled to a single conductive contact 76 on printed circuit 54. Sensor signals (e.g., temperature signals, pressure signals, humidity signals and sound signals) may be transmitted across components 64, 68, and 72 to contact 76. However, this is merely illustrative. If desired, one or more sensor components such as components 64, 68, and 72 may have dedicated electrical connections to printed circuit 54 as shown in FIG. 6.

Figure 6:
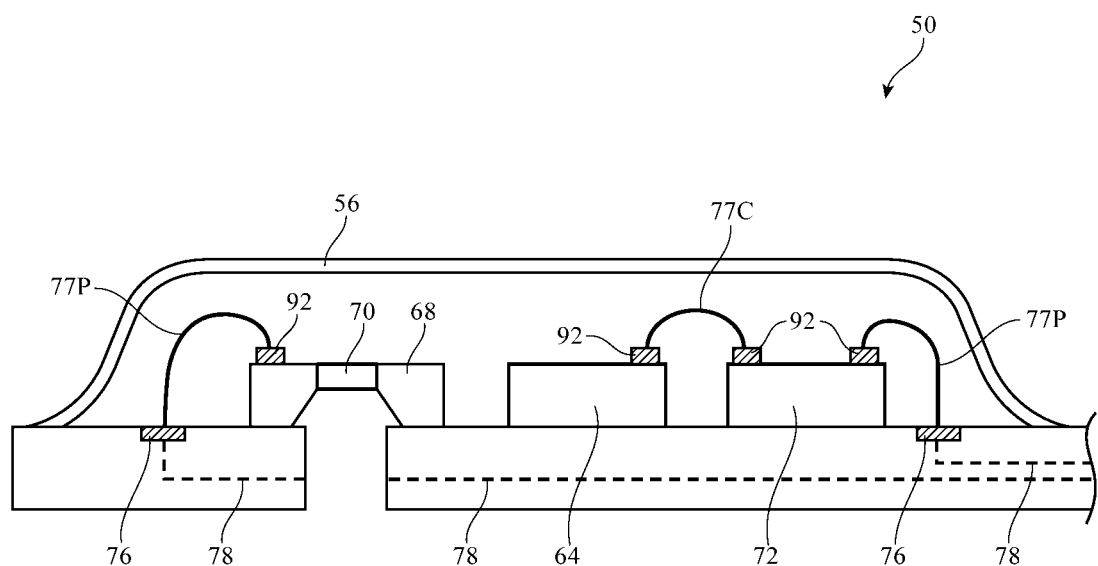
FIG. 6 is a cross-sectional side view of an illustrative environmental sensor having an opening in a printed circuit portion of the sensor showing how sensor components may be wire bonded to other sensor components and to multiple contact pads on the printed circuit portion of the sensor in accordance with an embodiment of the present invention.

In the example of FIG. 6, acoustic component 68 is coupled to a dedicated contact 76 using one of wire bonds 77P. In a configuration in which acoustic component 68 is coupled to a dedicated contact 76, component 64 may be coupled to component 72 using a wire bond 77C and component 72 may be coupled to an additional contact 76 using one of wire bonds 77P. However this is merely illustrative. If desired, each sensor component in sensor 50 may be coupled to a dedicated contact 76 on printed circuit 54 using wire bonds, solder, or other conductive coupling members or materials.

Figure 7:
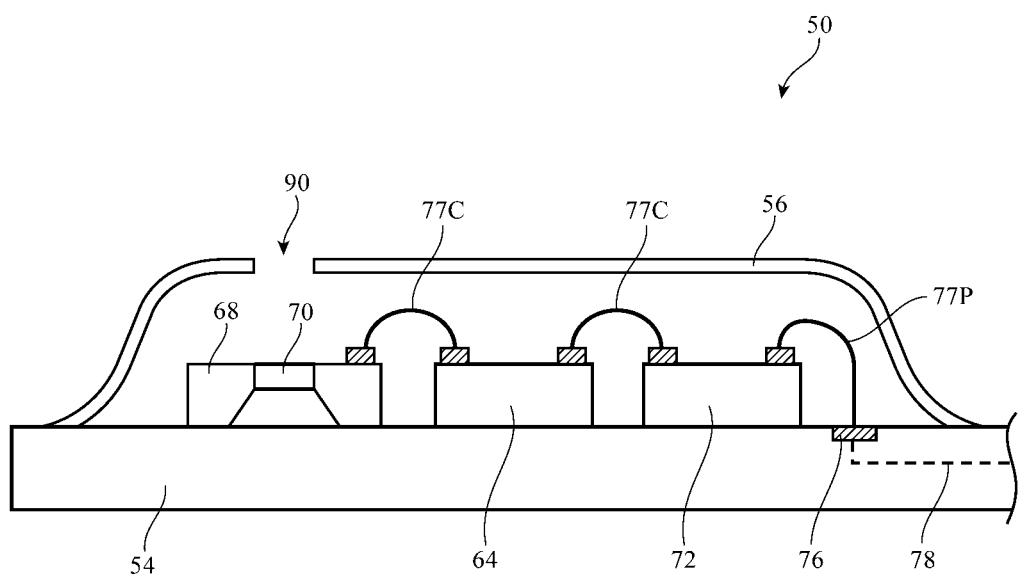
FIG. 7 is a cross-sectional side view of an illustrative environmental sensor having an opening in a rigid support structure of the sensor showing how sensor components may be wire bonded to other sensor components in accordance with an embodiment of the present invention.

FIG. 7 is a cross-sectional side view of environmental sensor 50 in a configuration in which sensor components such as components 64, 68, and 72 are covered by a rigid support structure 56 having an opening 90, showing how the sensor components may be coupled to each other and to the printed circuit using wire bonds 77. In the example of FIG. 7, membrane 70 of acoustic component 68 is aligned with opening 90, a wire bond 77C is coupled between contacts 92 on acoustic component 68 and sensor component 64 (e.g., a temperature sensor, a humidity sensor, or a temperature and humidity sensing integrated circuit), and an additional wire bond 77C is coupled between contacts 92 on sensor component 64 and sensor component 72 (e.g., a pressure sensor).

Figure 8:
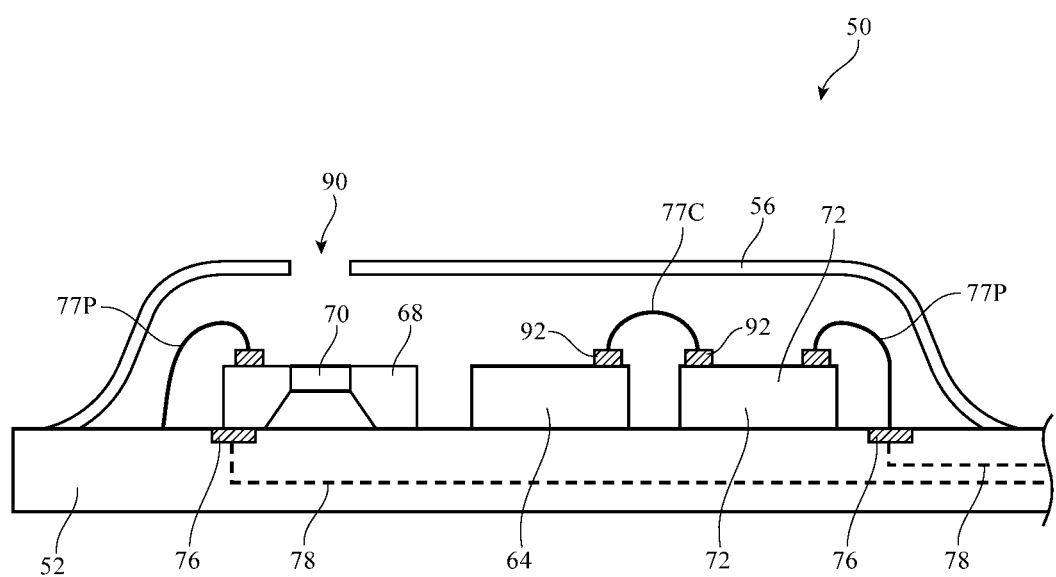
FIG. 8 is a cross-sectional side view of an illustrative environmental sensor having an opening in a rigid support structure of the sensor showing how sensor components may be wire bonded to other sensor components and to multiple contact pads on the printed circuit portion of the sensor in accordance with an embodiment of the present invention.

FIG. 8 is a cross-sectional side view of environmental sensor 50 in a configuration in which sensor components such as components 64, 68, and 72 are covered by a rigid support structure 56 having an opening 90, showing how one or more of components 64, 68, and 72 may have a dedicated electrical connection to printed circuit 54. In the example of FIG. 8, membrane 70 of acoustic component 68 is aligned with opening 90, acoustic component 68 is coupled to a dedicated contact 76, component 64 is coupled to component 72 using a wire bond 77C and component 72 is coupled to an additional contact 76 using one of wire bonds 77P. However this is merely illustrative. If desired, each sensor component in sensor 50 may be coupled to a dedicated contact 76 on printed circuit 54 using wire bonds, solder, or other conductive coupling members or materials.

If desired, sensor components for device 10 and environmental sensor 50 (e.g., sensor components 64, 68, 72, and/or other sensors) may include gas sensors, smoke detectors, and other sensors. Smoke sensors may measure particulates in the air that are indicative of the presence of a fire or other source of smoke. Gas sensors may, for example, be used to measure the concentration of carbon monoxide, carbon dioxide, alcohol vapor, water vapor (humidity), propane and other fuels, volatile organic compounds, ozone, nitric oxide, nitrogen dioxide, benzene, methane, hydrogen, oxygen, or other gases that are present in the atmosphere in the vicinity of device 10.

Sensor data may be gathered using one or more sensor components in environmental sensor 50. One or more sensor data processing circuits (i.e., application-specific integrated circuits) may be used in processing the sensor data.

For example, an audio sensor such as a microphone may produce analog microphone signals. These microphone signals may be processed using a sensor data processing integrated circuit with an analog amplifier and associated analog-to-digital converter circuitry. The analog amplifier may be used to amplify the sensor signals. The analog-to-digital converter circuitry may convert the amplified signals to digital form. Additional control circuits may, if desired, process the digital audio sensor data.

As another example, a gas sensor such as a sensor for detecting carbon monoxide or other gases may produce a gas sensor reading that is processed using a hardwired gas sensor data processing circuit in an integrated circuit. In some situations, the resources of multiple sensor components can be implemented on a common semiconductor die. For example, a microelectromechanical systems (MEMs) microphone and a gas sensor may be implemented on a common silicon die. By incorporating multiple components into a single part, cost and complexity may be minimized.

Figure 9:
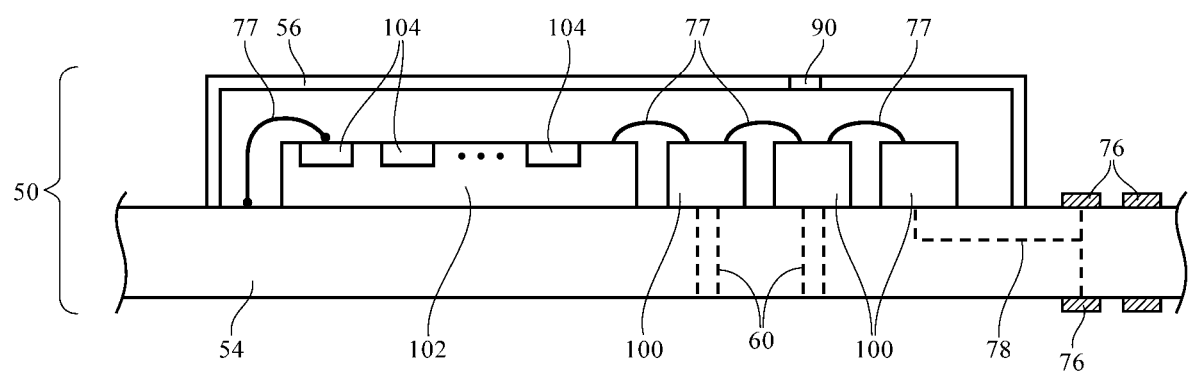
FIG. 9 is a cross-sectional side view of an illustrative environmental sensor having an integrated circuit that serves as a sensor data processing circuit for multiple associated sensor components in accordance with an embodiment.

Consider, as an example, illustrative environmental sensor 50 of FIG. 9. As shown in the example of FIG. 9, an opening such as opening 90 may be formed in structure 56 or an opening such as one or more openings 60 may be formed through a supporting substrate such as printed circuit board 54 to allow the environment surrounding sensor 50 to communicate with one or more components 100. Components 100 may include a pressure sensor, humidity sensor, temperature sensor, audio sensor (microphone), gas sensor, smoke detector, or other sensor(s). One or more processing circuits such as sensor data processing circuit 102 may be used in processing sensor data from sensor(s) 100. Sensor data processing circuit 102 and components 100 may be interconnected with each other and with external circuitry using signal paths formed from wire bonds 77 and/or printed circuit board paths 78. The signal paths of sensor 50 may be coupled to external components using contacts 76 on the upper and/or lower surfaces of printed circuit board 54 (as an example).

Sensor data processing circuit 102 may include one or more circuits (circuit blocks) such as circuits 104. Circuits 104 may include a communications interface block for supporting analog and/or digital signal communications between circuit 102 and external resources (e.g., communications with a system controller over a digital signal bus, etc.). Circuits 104 may also include sensor data processing blocks for one or more associated components 100. If, for example, components 100 include first, second, and third components, circuits 104 may include a first circuit for processing sensor data from the first component (e.g., hardwired gas sensor processing circuitry for processing signals from a gas sensor), a second circuit for processing sensor data from the second component (e.g., hardwired audio amplifier and analog-to-digital converter circuitry for handling audio data from a microphone), and a third circuit for processing sensor data from the third component (e.g., a temperature processing circuit for processing temperature sensor data from a temperature sensor). Components 100 and circuits 104 may also contain additional sensors and additional corresponding processing circuits, if desired (e.g., resources for sensing humidity, pressure, etc.).

If desired, circuits 102 may include a general purpose data processing block (e.g., a microcontroller circuit) for handling signal processing operations for one or more of components 100. Wire bonds 77 and/or printed circuit paths 78 may be used to couple each of components 100 directly to circuit 102 or one or more of components 100 may be coupled to circuit 102 through one or more intervening components 100.

Figure 10:
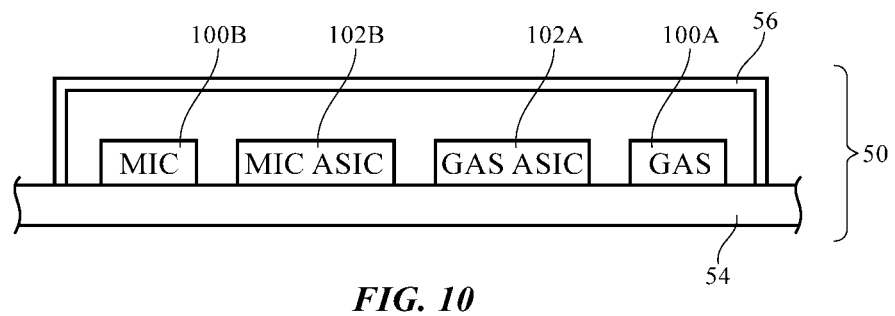
FIG. 10 is a cross-sectional side view of an illustrative environmental sensor having a microphone sensor data processing circuit that processes microphone sensor data from a stand-alone microphone and having a gas sensor data processing circuit that processes gas sensor data from a stand-alone gas sensor in accordance with an embodiment.

Multiple sensor components (sensors) and multiple associated sensor data processing circuits may be mounted within a common structure such as structure 56 of FIG. 10. For example, data processing circuit 102A (e.g., a gas sensor data processing circuit) may be used to process sensor data from sensor component 100A (e.g., a gas sensor) and data processing circuit 102B (e.g., a microphone data processing circuit) may be used to process sensor data from sensor component 100B (e.g., a microphone).

Figure 11:
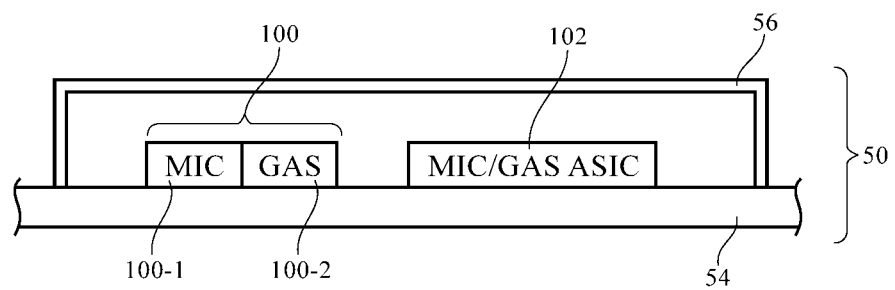
FIG. 11 is a cross-sectional side view of an illustrative environmental sensor having a single sensor data processing circuit that handles data from multiple sensors such as microphone and gas sensors that are formed from a common semiconductor die in accordance with an embodiment.

As shown in the illustrative configuration of FIG. 11, the functionality of multiple sensors may be implemented using a common semiconductor die (e.g., a shared silicon die). For example, sensor component 100-1 (e.g., a microphone) and sensor component 100-2 (e.g., a gas sensor) may both be formed as parts of common silicon die 100 (i.e., a single integrated circuit). Sensor processing circuits 104 for processing data from sensors 100-1 and 100-2 may also be implemented on a common semiconductor die such as shared silicon die 102 of FIG. 11, which may contain a first sensor data processing circuit 104 (e.g., a microphone data processing circuit) for processing data from sensor 100-1 and a second sensor data processing circuit 104 (e.g., a gas sensor data processing circuit) for processing data from sensor 100-2.

Figure 12:
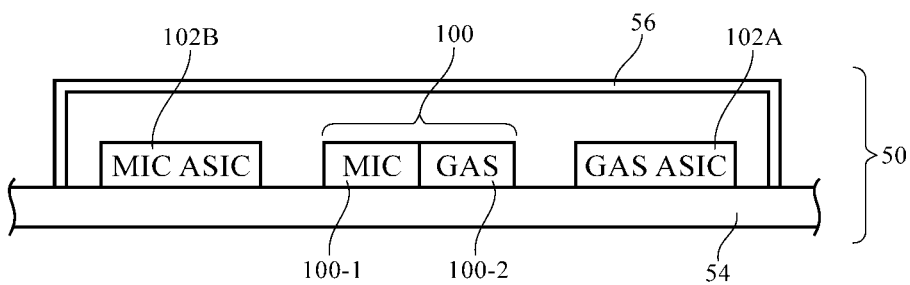
FIG. 12 is a cross-sectional side view of an illustrative environmental sensor having multiple sensor data processing circuits for handling data from multiple sensors integrated on a common semiconductor die in accordance with an embodiment.

FIG. 12 illustrates how multiple respective sensor data processing circuits such as circuits 102B (e.g., a microphone data processing circuit) and 102A (e.g., a gas sensor data processing circuit) may be used to process sensor data from a common die 100 that has been used to implement multiple respective sensor components 100-1 and 100-2 (e.g., microphone and gas sensor components, respectively).

In the examples of FIGS. 10, 11, and 12, two different types of sensors have been used in forming sensor 50. This is merely illustrative. Three or more sensors and sensors of any suitable types may be used as sensor components for sensor 50. Moreover, different packaging arrangements may be used in forming sensor packages for environmental sensor 50. The use of an upper structure such as a cowling to cover sensor components mounted to a lower structure such as a printed circuit is presented as an example.

If desired, data from one or more sensors may be used to refine or otherwise process data from one or more other sensors. For example, ambient pressure measurements may be used to adjust the way in which microphone measurements are made (e.g., to accommodate audio characteristics that change with changes in altitude).

Figure 13:
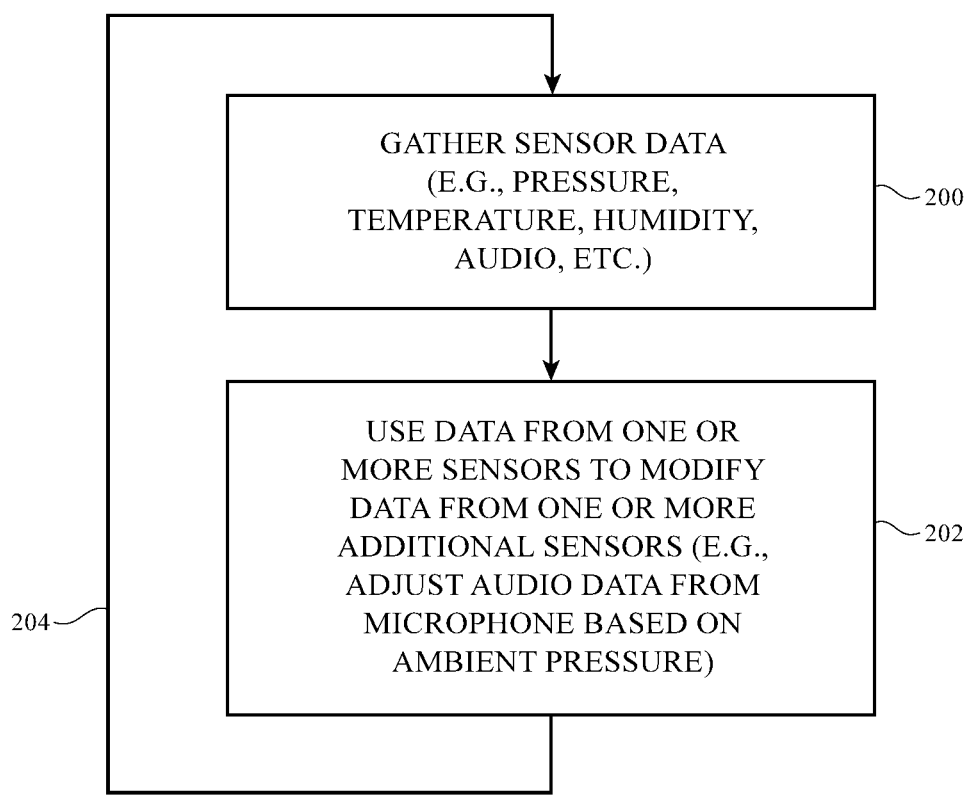
FIG. 13 is a flow chart of illustrative steps involved in gathering and processing sensor data in accordance with an embodiment.

A flow chart of illustrative steps involved in processing sensor data with sensor 50 is shown in FIG. 13.

At step 200, sensor data processing circuitry 104 (one or more integrated circuits) may gather sensor data from sensor components 100. Sensor components 100 may include microphone(s), gas sensor(s), pressure sensor(s), humidity sensor(s), temperature sensor(s), smoke detector(s), and/or other sensors.

At step 202, the sensor data that was gathered from one or more of the sensors may be used in processing the sensor data. For example, the sensor data that was gathered from one or more of the sensors may be used in processing the sensor data from one or more different sensors. Microphone data, gas sensor data, smoke detector data, temperature data, and/or pressure sensor data may be modified based on ambient pressure data, temperature data, humidity data, microphone data, smoke detector data, and/or other environmental data (as examples).

After processing the measured sensor data during the operations of step 202, device 10 may take suitable action based on the processed sensor data and processing may loop back to step 200, as indicated by line 204.

The foregoing is merely illustrative of the principles of this invention and various modifications can be made by those skilled in the art without departing from the scope and spirit of the invention. The foregoing embodiments may be implemented individually or in any combination.

What is claimed is:

1. A sensor package, comprising:
    a printed circuit;
    a rigid support structure attached to the printed circuit;
    a first environmental sensor attached to the printed circuit, wherein the rigid support structure and a portion of the printed circuit form an enclosure that surrounds the first environmental sensor; and
    an ambient light sensor mounted within the enclosure, wherein the enclosure comprises an opening that allows air to pass through the opening into the enclosure.

2. The sensor package defined in claim 1, wherein the first environmental sensor comprises a sensor selected from the group consisting of: a microphone, a gas sensor, a smoke detector, a pressure sensor, a temperature sensor, and a humidity sensor.

3. The sensor package defined in claim 1, wherein the first environmental sensor comprises a microphone.

4. The sensor package defined in claim 1, wherein the first environmental sensor comprises a gas sensor that is configured to measure a concentration of a gas.

5. The sensor package defined in claim 4, wherein the gas comprises a gas selected from the group consisting of: carbon monoxide, carbon dioxide, alcohol vapor, propane, ozone, nitric oxide, nitrogen dioxide, benzene, methane, hydrogen, and oxygen.

6. The sensor package defined in claim 1, wherein the opening comprises an opening in the rigid support structure.

7. The sensor package defined in claim 1, wherein the opening comprises an opening in the printed circuit.

8. The sensor package defined in claim 1, wherein the first environmental sensor comprises a permeable membrane, wherein the opening is aligned with the permeable membrane, and wherein air passes through the opening and the permeable membrane into the enclosure.

9. A sensor package, comprising:
a printed circuit;
a rigid support structure attached to the printed circuit;
a first sensor that is attached to the printed circuit;
a second sensor that is attached to the printed circuit, wherein the rigid support structure and a portion of the printed circuit form an enclosure that surrounds the first and second sensors, wherein the enclosure comprises an opening that allows air to pass through the opening into the enclosure; and
a semiconductor die that is attached to the printed circuit and that includes both a first sensor data processing circuit that processes first sensor data from the first sensor and a second sensor data processing circuit that processes second sensor data from the second sensor.

10. The sensor package defined in claim 9, wherein the semiconductor die is a first semiconductor die, wherein the first sensor is formed from a second semiconductor die and the second sensor is formed from a third semiconductor die.

11. The sensor package defined in claim 9, further comprising a first wire bond between the semiconductor die and the first sensor and a second wire bond between the first sensor and the second sensor.

12. The sensor package defined in claim 9, further comprising a first wire bond between the semiconductor die and the first sensor and a second wire bond between the semiconductor die and the second sensor.

13. The sensor package defined in claim 9, wherein the first sensor comprises a sensor selected from the group consisting of: a microphone, a gas sensor, a smoke detector, a pressure sensor, a temperature sensor, and a humidity sensor and wherein the second sensor comprises a sensor selected from the group consisting of: a microphone, a gas sensor, a smoke detector, a pressure sensor, a temperature sensor, and a humidity sensor.

14. The sensor package defined in claim 9, wherein the first and second sensors are formed from a common semiconductor die.

15. The sensor package defined in claim 14, wherein the first sensor comprises a microphone and the second sensor comprises a gas sensor.

16. The sensor package defined in claim 15, wherein the gas sensor is configured to measure a concentration of a gas and wherein the gas comprises a gas selected from the group consisting of: carbon monoxide, carbon dioxide, alcohol vapor, propane, ozone, nitric oxide, nitrogen dioxide, benzene, methane, hydrogen, and oxygen.

17. An electronic device comprising:
a housing having a first opening;
a printed circuit having a second opening;
a rigid support structure attached to the printed circuit;
a first sensor attached to the printed circuit; and
a second sensor attached to the printed circuit, wherein the rigid support structure and a portion of the printed circuit form an enclosure that surrounds the first and second sensors and wherein air passes through the first and second openings into the enclosure.

18. The electronic device defined in claim 17, wherein the second opening is aligned with the first opening.

19. The electronic device defined in claim 17, further comprising:
mesh that covers that first opening.

20. The electronic device defined in claim 17, wherein the first sensor comprises a sensor selected from the group consisting of: a microphone, a gas sensor, a smoke detector, a pressure sensor, a temperature sensor, and a humidity sensor and wherein the second sensor comprises a sensor selected from the group consisting of: a microphone, a gas sensor, a smoke detector, a pressure sensor, a temperature sensor, and a humidity sensor.

* * * * *